United States Patent [19]

Pettit et al.

[11] Patent Number: 4,477,187

[45] Date of Patent: Oct. 16, 1984

[54] APPARATUS AND METHOD FOR SIZING PARTICLES

[75] Inventors: Donald R. Pettit; Thomas W. Peterson, both of Tucson, Ariz.

[73] Assignee: University Patents, Inc., Norwalk, Conn.

[21] Appl. No.: 342,539

[22] Filed: Jan. 25, 1982

[51] Int. Cl.$^3$ .............................................. G01B 9/05
[52] U.S. Cl. ..................................... 356/335; 356/349
[58] Field of Search ........................ 356/335, 349, 360

[56] References Cited

U.S. PATENT DOCUMENTS 3,539,262 11/1970 Pryor .............................. 356/349 X
4,097,153 6/1978 DeRemigis ..................... 356/349 X Primary Examiner—Davis L. Willis
Assistant Examiner—Matthew W. Koren
Attorney, Agent, or Firm—Martin Novack

[57] ABSTRACT

The disclosed invention employs an optical heterodyne technique that depends upon coherent detection of phase modulated light from individual particles, and does not depend on measurement of light scattered at a specific angle from particles. A collimated coherent beam of light is generated and separated into a subject beam and a reference beam. The subject beam is focused at the inspection region and light is gathered from the inspection region. The gathered light and the reference beam are combined and a photodetector is responsive to the combined light for producing an electrical signal representative of the combined light. The phase shift of light scattered from an individual particle passing through the inspection region is then determined by measuring the power in the phase modulated sidebands of the electrical signal. The phase shift is indicative of the size of the particle passing through the inspection region.

19 Claims, 8 Drawing Figures

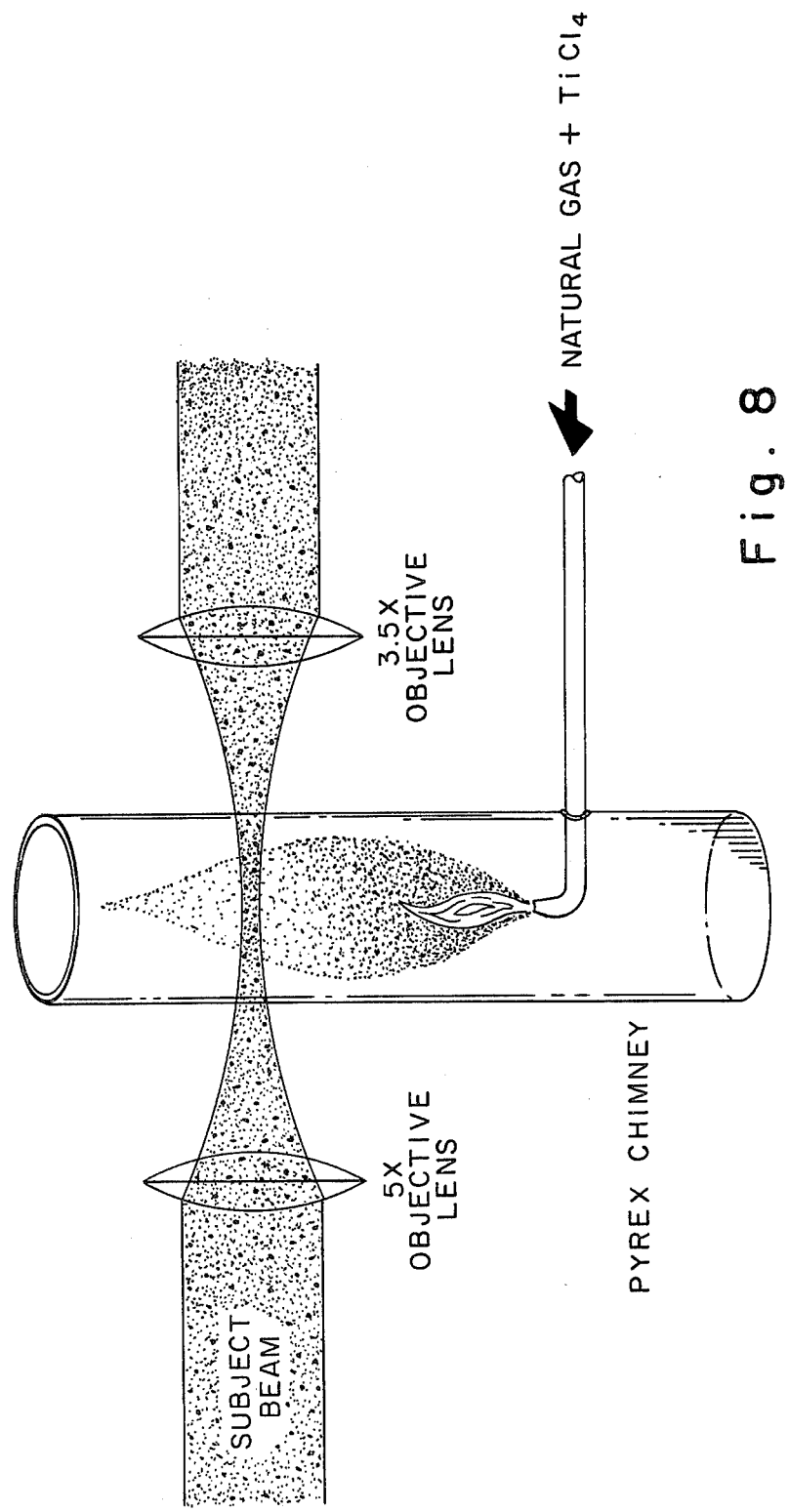

APPARATUS AND METHOD FOR SIZING PARTICLES

BACKGROUND OF THE INVENTION

This invention relates to particle measurement techniques and, more particularly, to an apparatus and method for sizing and counting particles.

Airborne particulate matter, such as industrial aerosols and combustion-generated aerosols, generally span a range of particle diameters from about 0.001 to 10 micrometers ($\mu$m). Because of the variable effect of particle size on visibility degradation, health, in-plant corrosion and so forth, it is advantageous to determine not only the total aerosol burden suspended in a gaseous medium (e.g., the number $\mu g/m^3$ of all suspended material), but the size distribution of that suspended material as well.

Currently, there is no adequate single technique available for continuously determining the size distribution of aerosols over the entire range of interest. Typically two instruments are utilized to span this range. For particles between about $10^{-3}$ and 1.0 $\mu$m, particle size may be determined based on the electrical mobility of the particle, the instrument most often used for measurements of this type being the so-called "electrical aerosol analyzer". In this instrument, aerosol is first exposed to unipolar gaseous ions in a diffusion charger. The electrical mobility of the aerosol is then ascertained, from which the size distribution is then calculated. The upper limit of particle detection by this instrument is typically about 1.0 $\mu$m.

A variety of optical detection techniques have been utilized in determining particles greater than about 0.1 $\mu$m diameter. Both monochromatic and polychromatic light sources have been employed, as have a wide range of detection systems. Descriptions of optical detection methods are set forth, for example, in review articles that can be found in Optical Engineering, Vol. 19, No. 6 (1980).

Two separate instruments utilizing different principles of operation are accordingly needed in the prior art to determine the size distribution of suspended airborne particulate matter. It is among the objects of the present invention to develop a single particle counting apparatus and method which can measure particles over the entire size range of interest. A further object of the invention is to develop a technique to measure particle concentrations typical of atmospheric or industrial particle loadings. A still further object of the invention is to develop a technique which has application for in-situ measurement conditions.

SUMMARY OF THE INVENTION

The present invention employs an optical heterodyne technique that depends upon coherent detection of phase modulated light from individual particles, and does not depend on measurement of light scattered at a specific angle from particles. In particular, the present invention is directed to an apparatus and method for sizing individual particles passing through an inspection region. In accordance with the apparatus of the invention, there is provided a means for generating a collimated coherent beam of light. The beam is separated into a subject beam and a reference beam (or local oscillator beam). Means are provided for focusing the subject beam at the inspection region. Light is gathered from the inspection region, and means are provided for combining the gathered light and the reference beam. A photodetector is responsive to the combined light for producing an electrical signal representative of the combined light. Means are then provided for determining the phase shift of light scattered from an individual particle passing through the inspection region by measuring the power in the phase modulated sidebands of the electrical signal. The phase shift is indicative of the size of the particle passing through the inspection region.

Preferably, the gathered light will include only near-forward light, which is defined herein as light collected along the axis of the subject beam and at angles within about plus or minus twenty-five degrees from said axis.

In a form of the invention, the number of pulses which occur per unit time is also counted.

The present invention has the advantage of allowing sizing of particles over a wide range of sizes with a single technique. Also, the invention can be adapted for in-situ measurement conditions.

Further features and advantages of the invention will become more readily apparent from the following detailed description when taken in conjunction with the accompanying drawings.

BRIEF DESCRIPTION OF THE DRAWINGS

FIG. 8 illustrates a setup used to test the in-situ capabilities of an embodiment of the invention.

DESCRIPTION OF THE PREFERRED EMBODIMENT

Figure 1:
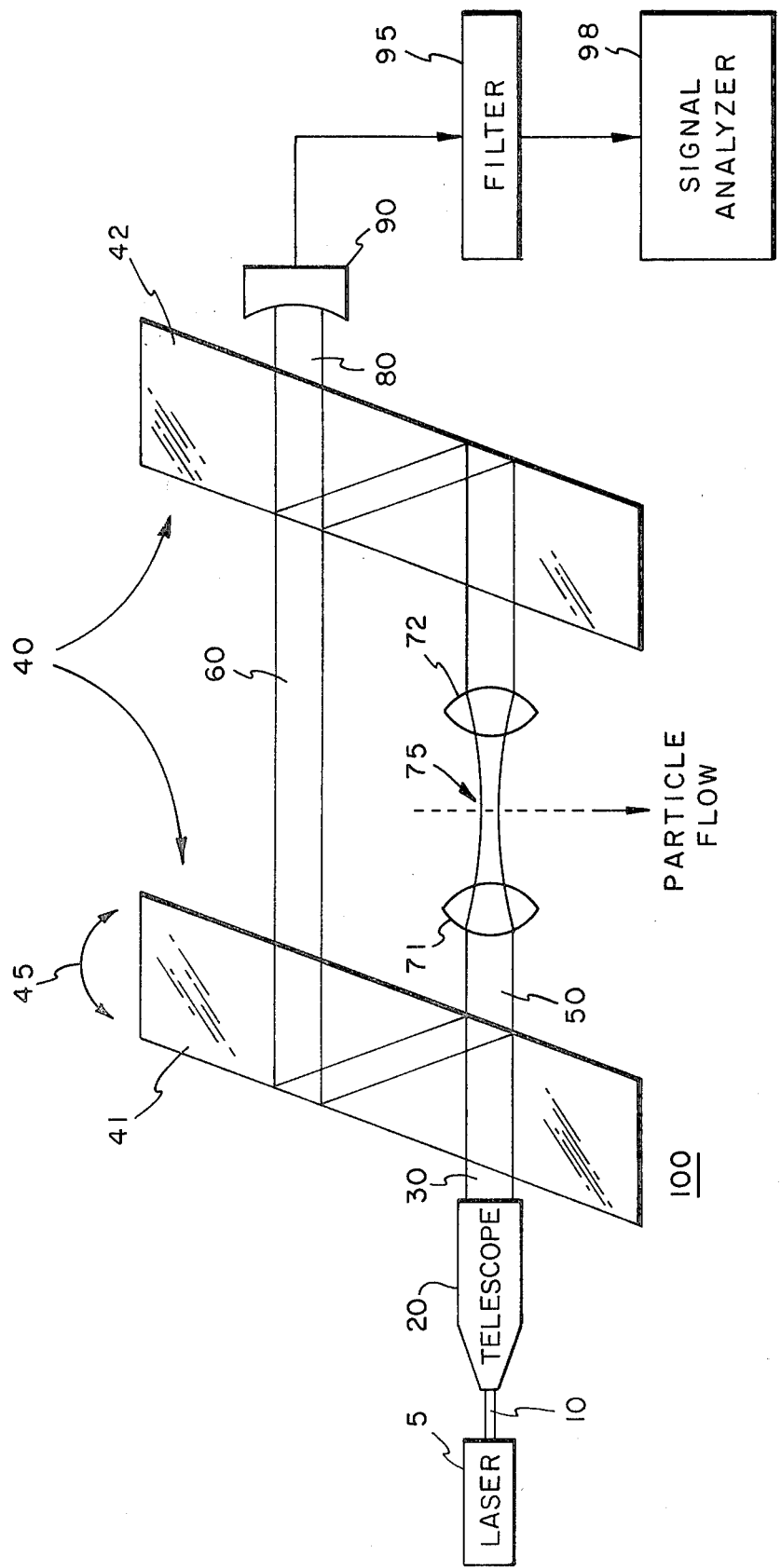
FIG. 1 is a block diagram, partially in schematic form, of an apparatus in accordance with an embodiment of the invention, and which can be used to practice the method of the invention.

Referring to FIG. 1, there is shown an apparatus 100 in accordance with an embodiment of the invention and which can be used to practice the method of the invention. A laser 5 generates a laser beam 10 that is expanded by a telescope 20 to obtain an expanded collimated and coherent light beam 30. A Jamin interferometer 40 includes spaced prisms 41 and 42. The prism 41 divides the beam 30 into a subject beam 50 and a reference beam 60. The reference beam 60, also sometimes referred to as a local oscillator beam, can conventionally be phase adjusted by movement of prism 41, as represented by arrows 45. In the path of the subject beam 50 are a spaced pair of lenses 71 and 72 that are arranged so that the beam emerging from the lens 72 remains collimated. In particular, in the present embodiment an inspection region 75 is defined as being at the focus of the primary lens 71. The region 75 is also spaced from the location of gathering lens 72 by the focal length of said lens 72. The collimated beam emerging from the gathering lens 72 is combined with the reference beam 60 by prism 42, and the combined beam 80 is received by photodetector 90. The output of photodetector 90 is coupled to filter 95, whose output is, in turn, coupled to signal analyzer 98. Signal analyzer 98 may be any suitable circuitry for measuring the power in the phase modulated sidebands of the electrical signal. The signal analyzer 98 may comprise a multichannel analyzer, for example, a Model 1024D Multichannel Analyzer sold by The Nucleus, Inc. of Oak Ridge, Tenn.

The theory of detection of particles at the inspection region will now be discussed. If a single particle is allowed to scatter light at the focal point of a lens the van Cittert-Zernicke conditions [see e.g. Born et al., "Principles of Optics", Pergamon (1959) and Gould et al., Applied Optics, 3(5), 648 (1964)] show that the gathered light will be coherent if the scattering is contained in a region smaller than the resolution limit of the gathering lens. This gathered light will exhibit an average phase shift determined by the solid angle of view of the lens. Applicants have discovered that if the gathered light beam is coherently superimposed with a reference beam upon a shot-noise-limited square law detector (e.g. implemented by the photodetector) the power in the phase shifted side bands can be measured and related (via scattering mechanisms) to the particle diameter.

The local oscillator beam 60, with adjustable relative phase, passes undisturbed to the photodetector. Consider monodisperse single spherical particles passing at a constant rate through the beam waist 75 (which contains the inspection region) perpendicular to the optical axis. As stated, if the particle is smaller than the resolution limit of the second lens, the gathered light will be coherent, as specified by the van Cittert Zernicke conditions, and will contain average phase shift information determined by the solid angle of view. After the subject beam is coherently superimposed with the local oscillator at the photodetector, the subject beam will be phase modulated by the particles at a frequency equal to the rate of particles passing through the beam waist, and can thus be detected using an optical heterodyne technique.

Since the present technique is based on measuring single particles as they pass through an optical viewing volume (the inspection region 75), it is important to define the radial and axial extent of this viewing volume. It would be desirable to have a viewing volume such that any particle contained inside will give the same signal regardless of its internal position or trajectory, with the boundaries of the region being sharply defined.

Figure 2:
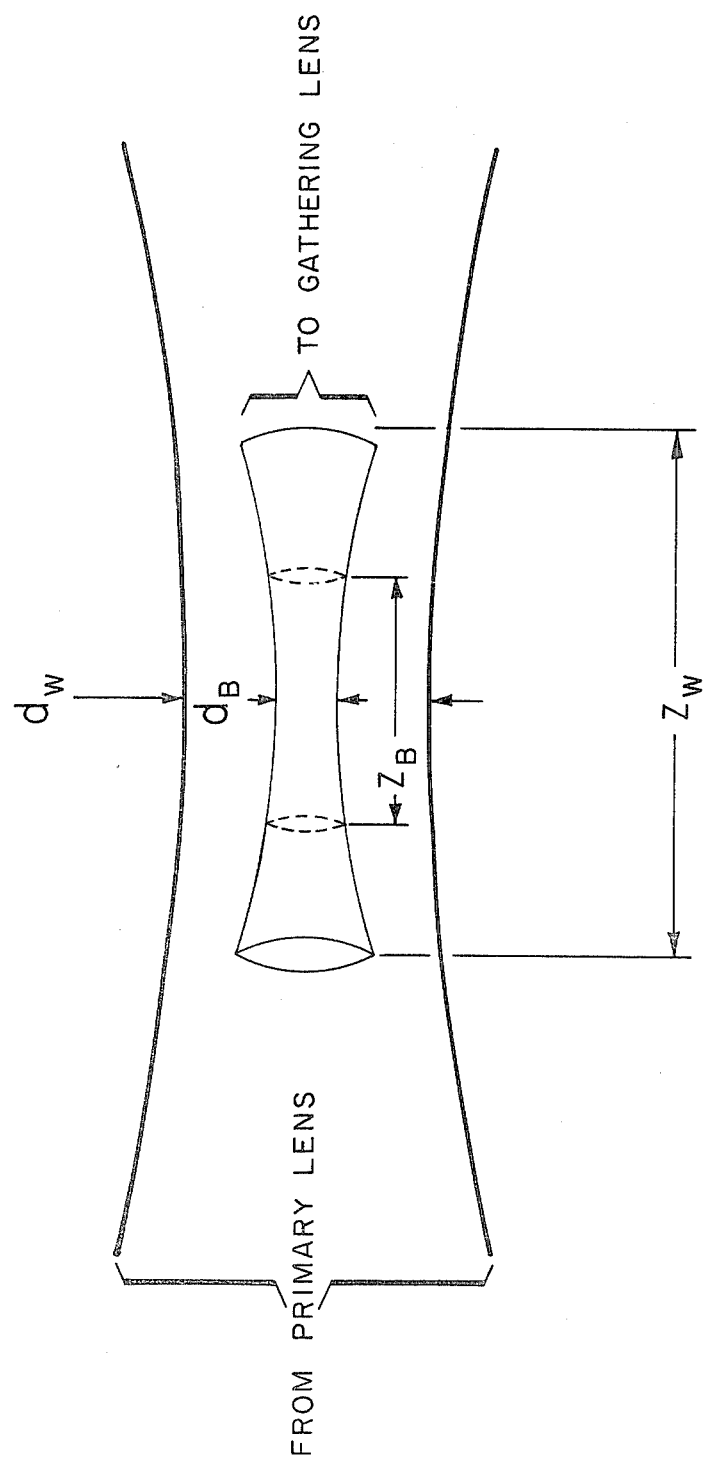
FIG. 2 is a diagram useful in describing parameters of the inspection region of the FIG. 1 embodiment.

The physical geometry of the optical viewing volume for the system is shown in FIG. 2. A Gaussian beam waist is provided by the primary lens, which has an aperture large enough to pass the power in the subject beam. The light is focused to a waist diameter $d_w$, defined by the $e^{-\pi}$ wave field amplitude point. The axial waist length $Z_w$ is the collimated portion of the beam and extends one Rayleigh length in each direction from the beam waist. The Rayleigh length is the distance where the beam spreads to $\sqrt{2}$ times the beam waist diameter. The gathering lens is responsible for defining the limits of the viewing volume with its depth of focus and resolution-limited blur spot diameter, $d_B$. Phase shifted light by particles within $d_B$ will not be resolved into independent wave fronts and will appear as coherent plane waves downstream of the gathering lens, as shown by the van Cittert-Zernike theorem.

The radial extent of the viewing volume will be determined by $d_B$. Phase shifted light from particles within this zone will be imaged as coherent plane waves propagating down the optical axis that are parallel and coincident with the local oscillator beam 60. Light scattered by particles radially outside this zone will be imaged as coherent plane waves propagating at an angle to the optical axis and will not be measured by the coherent detection methods hereof.

The axial extent of the zone where the van Cittert-Zernike theorem applies will be determined by the depth of focus of the gathering lens. The axial extent of the optical viewing volume, $Z_B$, extends plus and minus one depth of focus from the focal point. Phase shifted light from particles to the right of the axial region will not be imaged as coherent plane waves, and will not contribute to signals measured by the coherent detection techniques. Particles to the left of this axial region will likewise impart a phase shift, with a portion of this light propagating forward into the optical viewing volume and being imaged as coherent plane waves, extending the axial distance of the viewing volume somewhat further to the left of the focal point than one depth of focus.

In order to assure a signal that is substantially independent of particle position within the viewing volume, a substantially uniform intensity of incident light should exist throughout. This can be achieved by coordinating the geometry of $d_w$ and $Z_w$ from the primary lens with $d_B$ and $Z_B$ from the gathering lens. The intensity within the viewing volume will be given by $I(z,r)$ where z and r denote axial and radial coordinates from the origin at the beam waist.

The radial intensity across the beam at any position z is Gaussian and can be described [see Gaskill, J. D., "Linear Systems, Fourier Transforms, and Optics", Wiley & Sons, 1978] as:

$$\frac{I(z,r)}{I(z,o)} = \exp\left\{-2\pi\left(\frac{r}{b}\right)^2\right\} \quad (1)$$

where
 r = radial distance from centerline;
 b = Gaussian beam radius to $e^{-\pi}$ point in wave field amplitude;
 I(z,o) = centerline intensity at position z.

If $d_B$ is centered in $d_w$ and $(d_B/d_w) \leq 0.1$, then the radial intensity profile incident on $d_B$ will not vary more than 6% and can be assumed sufficiently uniform to be constant in the radial direction. The axial intensity at centerline is given by:

$$\frac{I(z,o)}{I(o,o)} = \left(\frac{d_w}{d_z}\right)^2 \quad (2)$$

where
 $d_w$ = diameter at beam waist to $e^{-\pi}$ point in wave field amplitude;
 $d_z$ = beam diameter to $e^{-\pi}$ point at axial position z from beam waist;
 I(o,o) = centerline intensity at beam waist.

The beam diameter at axial position z from the waist is given by:

$$d_z = d_w \sqrt{1 + (z/Z_R)^2} \quad (3)$$

-continued where $Z_R$ = Rayleigh length = $\frac{d_w^2}{4\lambda}$.

Let axial position z be defined as a fraction of the Rayleigh length, so that:

$$z = Z_R/\gamma \quad (4)$$

where $1/\gamma$ = fraction of Rayleigh length from beam waist, then Equations (2) through (4) yield:

$$\frac{I(z,o)}{I(o,o)} = \frac{1}{1 + \left(\frac{1}{\gamma}\right)^2} \quad (5)$$

From Equation (5), if $d_w$ and $d_B$ axially coincide with $Z_B \leq (Z_R/5)$, then the axial centerline intensity profile within $Z_B$ will not vary more than 1% and therefore will not compound the radial intensity profile error.

The integrated power from centerline to radial position r is given as:

$$\frac{P(r)}{P_{tot}} = 1 - \exp\left\{-\frac{\pi}{2}\left(\frac{r}{b}\right)^2\right\} \quad (6)$$

where
r = radial position from centerline;
b = beam radius to $e^{-\pi}$ in wave field amplitude;
$P_{tot}$ = total power in the beam.

For the case of constant radial intensity ($d_B/d_w = 0.1$), only 1.56% of the total beam power is contained within the blur spot diameter $d_B$ and therefore contributes to particle measurement.

It is difficult to construct an optical viewing volume where the edges are defined by sharp boundaries. There will generally be a "fuzzy zone" surrounding the edges so particles of a given diameter that happen to pass close to a boundary will result in a different signal than those that pass directly through. It is desirable to minimize this fuzzy zone so particle counting errors are small.

The radial edges of the viewing volume are determined by the degree of nonparallelism between the scattered light and the local oscillator beam. Coherent detection methods are quite sensitive to misalignment, giving a rather sharp radial boundary. The axial distance of the photodetector from the interferometer will affect this sensitivity.

The trailing edge of the viewing volume will be sharply defined by the depth of focus where the van Cittert-Zernike theorem applies. The leading edge will be the fuzziest boundary because particles further to the left will phase shift light that could propagate forward into the viewing volume and be counted as smaller particles.

Consider the following example for specifying the design of the viewing volume. The radial diameter ($d_B$) should be substantially greater (preferably, at least 5 times greater) than the maximum particle diameter $(d_p)_{max}$. This will minimize near-miss errors, wherein the particle straddles a boundary and is only partially contained within the viewing volume. For a $(d_p)_{max}$ of 5 $\mu$m, a $d_B$ of 25 $\mu$m would be sufficient. Once a gathering lens with a given $d_B$ is specified, the depth of focus is determined. For $d_B$ of 25 $\mu$m, a corresponding $Z_B$ of 100 $\mu$m is typical [See Driscoll, W. G., "Handbook of Optics", McGraw Hill, 1978]. To insure a uniform radial intensity within $d_B$, $d_w$ must be 250 $\mu$m. The corresponding Rayleigh length for a He-Ne laser with this beam waist is 26 mm, thus requiring $Z_B$ to be less than or equal to 5.2 mm. This is true for the above case.

The signals generated by uniformly spaced monodisperse aerosols passing through the viewing volume can be examined in either the time or frequency domain. In the time domain, pulses will occur with spacings given by the interval between particles passing through the beam. The pulse height will be given by the power measured in the phase-modulated side bands. The power in the phase-modulated side bands is related to the magnitude of the phase shift, which in turn can be related to the particle diameter.

Figure 3:
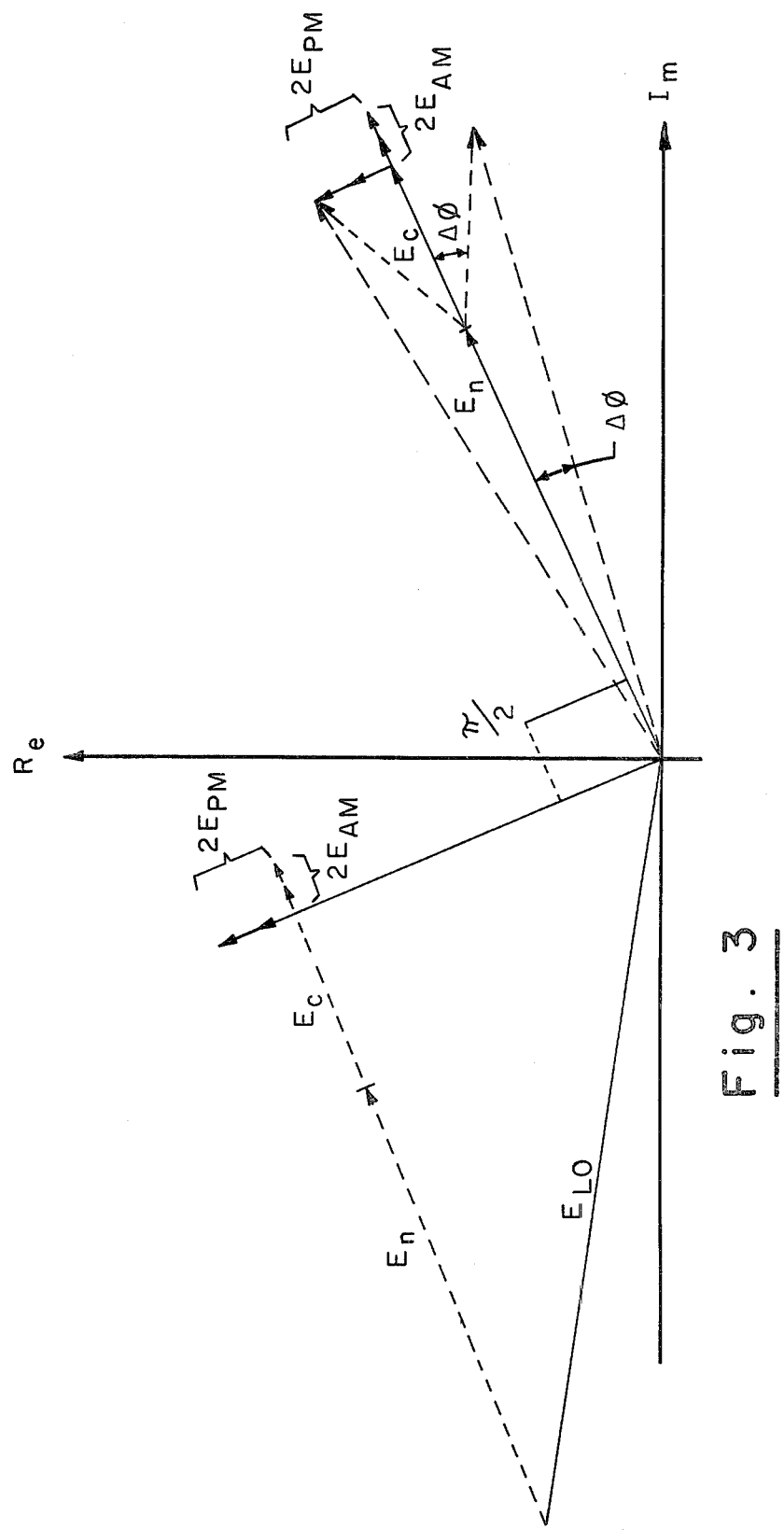
FIG. 3 is a phasor diagram which illustrates the phase modulation process.

The phase modulation process can be illustrated with a phasor diagram as shown in FIG. 3. The subject beam with power $P_s$ and electric field $E_s$ is subdivided into the carrier beam of power $P_c$ with electric field of $E_c$, which is the light incident on the scattering cross sectional area of the particle, and the noncarrier with power $P_n$ and electric field of $E_n$. The total power in the subject beam $P_s$ is equal to the sum of $P_n$ and $P_c$. The electric fields $E_n$ and $E_c$ are shown as phasors in FIG. 3 where the phase shift $\Delta\phi$ is due to $E_c$ incident on the particle and is approximated by two side-bands each with electric field $E_{pm}$ that rotate in opposite directions at the modulation frequency $\omega$. This rotation results in $E_c$ swinging through an arc given by particle phase shift $\Delta\phi$, causing the carrier to be phase modulated. For small angle modulation, the phase shift can be represented sufficiently by two side bands. Since $E_c$ and $E_n$ have identical phase, the resultant phase shift $\Delta\phi$ (which is the phase shift measured by the technique of the embodiment hereof) will be the vector sum of $E_c$, $E_n$ and $E_{pm}$. In addition to the phase modulated side bands, there will be amplitude modulated side bands $E_{am}$, due to scattering and absorption, rotating at the same frequency but resulting in their sum changing the length of $E_c$.

The local oscillator beam with power $P_{LO}$ and electric field $E_{LO}$ is adjusted so the phase of the resultant vector $E_r$ (given by the sum of $E_c$, $E_n$, $E_{pm}$, $E_{am}$, and $E_{LO}$) is in quadrature to the carrier $E_c$. When $E_r$ differs in phase from $E_c$ by $\pi/2$, then the phase modulated side bands on the carrier will appear as amplitude modulated side bands on the resultant, and the amplitude modulated side bands on $E_c$ will appear as phase modulated side bands on $E_r$ (see FIG. 3). In this way, it is possible for a photodetector to be used in measuring the power in the phase modulated side bands in terms of amplitude fluctuations, without detecting any effect from the amplitude modulation. The power in the side bands $P_{pm}$ can be found by considering small angle modulation, where:

$$E_{pm} \simeq \frac{(E_n + E_c)}{2} \Delta\phi' \quad (7)$$

Since we detect the power in both side bands together $$P_{pm} \simeq \frac{(E_n + E_c)^2}{2} (\Delta\phi')^2 \quad (8)$$

where $P_{pm}$ is the power in both phase modulated side bands.

For small angle modulation, the resultant phase shift in the subject beam $\Delta\phi'$ can be related to the phase shift due to the particle $\Delta\phi$ by:

$$\Delta\phi' \simeq \frac{E_c}{E_c + E_n} \Delta\phi \quad (9)$$

Substituting for $\Delta\phi'$ yields:

$$P_{pm} = \frac{\Delta\phi^2 P_c}{2} \quad (10)$$

Hence, the power in the phase modulated side bands is due to the magnitude of the particle phase shift $\Delta\phi$ and the power in the carrier. The power in $P_n$ does not interfere with the detection of the phase modulated side bands because it is in phase with $P_c$ and is balanced by the local oscillator when in quadrature.

To determine the theoretical signal as a function of particle size, the signal-to-noise ratio expression for a shot-noise-limited photodetector is used. For optical heterodyne detection, this is given [see Jacobs, S., Electronics, 29, July, 1963] as:

$$(S/N)_p = \frac{\eta P}{h\nu \Delta f} \quad (11)$$

where
 $\eta$=photodetector quantum efficiency;
 h=Planck's constant;
where
 $\nu$=frequency of carrier light;
 $\Delta f$=band width of electronics in signal processor;
 P=power in signal that is being measured;
 $(S/N)_p$=power signal to noise ratio, For phase modulation, P is equal to the power in the phase modulated side bands and is given by Equation (10).

The signal-to-noise ratio expression then becomes:

$$(S/N)_p = \frac{\eta \Delta\phi^2 P_c}{2h\nu \Delta f} \quad (12)$$

When the particle is inside the optical viewing volume, the incident intensity will be uniform, so the power in the carrier is given by:

$$P_c = P_B \frac{C_{scat}}{\pi/4 d_B^2} \quad (13)$$

where
 $P_B$=power contained within $d_B$;
 $C_{scat}$=particle scattering cross section.

For the conditions of small angle modulation, the particles would be in the Rayleigh scattering regime so the scattering cross section is given [see Kerker, M., "The Scattering of Light and Other Electromagnetic Radiation", Academic Press, 1969] as:

$$C_{scat} = \frac{24\pi^3 V^2}{\lambda^4} \left( \frac{n^2 - 1}{n^2 + 2} \right)^2 \quad (14)$$

where
 V=particle volume=$\pi/6\, d_p^3$;
 n=particle refractive index;
 $\lambda$=wavelength of light;
 $d_p$=particle diameter.

Using equation (6) to find $P_B$ results in:

$$P_B = P_s \left[ 1 - \exp\left\{ -\frac{\pi}{2}\left(\frac{d_B}{d_w}\right)^2 \right\} \right] \quad (15)$$

where $P_s$=power in subject beam.
$P_s$ will be approximately one half the total power of the laser, depending on the reflection losses from the interferometer. Combining Equations (12) through (15) gives:

$$(S/N)_p = \frac{4\eta \Delta\phi^2 d_p^6 P_s \left[ 1 - \exp\left\{ -\frac{\pi}{2}\left(\frac{d_B}{d_w}\right)^2 \right\} \right]}{3 h\nu \Delta f\, d_B^2} \left(\frac{\pi}{\lambda}\right)^4 \left(\frac{n^2 - 1}{n^2 + 2}\right)^2 \quad (16)$$

The particle phase shift, $\Delta\phi$, is a function of particle diameter and refractive index and can be determined rigorously by numerical solution of the scattering equations [See Wiscombe, W. J., Appl. Optics 19(9), 1505 (1980), and Fymat et al., Appl. Optics, 20(2), 194, (1981)]. Equation (16) assumes $d_B/d_w \leq 0.1$ for uniform intensity profiles and is limited to Rayleigh particles for scattering cross section and small angle modulation, where the phase shift can be represented by two side bands. These latter requirements make equation (16) useful for estimating the minimum detectable particle size.

Using Equation (16) to estimate the minimum detectable particle size, consider nonabsorbing spherical particles passing singly through the beam waist perpendicular to the optical axis. If an estimate for the minimum detectable particle is all that is desired, then the particle phase shift can be taken as the order of:

$$\Delta\phi = \frac{2\pi(n-1)d_p}{\lambda} \quad (17)$$

Combining Equations (16) and (17), and introducing a factor $\alpha$ to account for the amount of phase shifted light collected by the gathering lens yields:

$$(S/N)_p = \frac{16\eta a d_p^8 P_s \left[1 - \exp\left\{-\frac{\pi}{2}\left(\frac{d_B}{d_w}\right)^2\right\}\right]}{3h\nu\Delta f} \left(\frac{\pi}{\lambda}\right)^6 \left[\frac{n-1}{d_B}\right]^2 \left(\frac{n^2-1}{n^2+2}\right)^2 \quad (18)$$

where $a$ = fraction of phase shifted light collected by gathering lens.

Equation (18) can be used to estimate the minimum detectable particle size by selecting suitable values for the parameters indicative of experimental conditions. Typical values for the parameters that are fixed are:

| | | |
|---|---|---|
| silicon photodiode: | $\eta = .50$; | |
| lens components: | $\alpha = .10$ | (ten percent of phase shifted light collected); |
| | $(d_B/d_w) = .1$ | (to insure uniform radical intensity); |
| particles: | $n = 1.5$. | |

Parameters that are somewhat flexible and can fall over a range of values are $\Delta f$, $d_B$ and $P_s$. By rearranging Equation (18) and requiring the S/N ratio to be greater than one, a range of $(d_p)_{min}$ can be obtained for various values of these parameters, as given in the following Table I:

TABLE I

Estimates of Minimum Detectable Particle Size for Various $d_B$, $P_s$ and $\Delta f$

| $d_B[\mu m]$ | $(d_p)_{max}[\mu m]$ | $P_s$ | $\Delta f$[Hz] | $(d_p)_{min}[\mu m]$ |
|---|---|---|---|---|
| 2 | ≈.4 | 1 W | 1 | .005 |
| | | 1 W | 20 K | .02 |
| | | 5 mW | 1 | .01 |
| | | 5 mW | 20 K | .04 |
| 5 | ≈1. | 1 W | 1 | .007 |
| | | 1 W | 20 K | .02 |
| | | 5 mW | 1 | .01 |
| | | 5 mW | 20 K | .05 |
| 25 | ≈5 | 1 W | 1 | .01 |
| | | 1 W | 20 K | .04 |
| | | 5 mW | 1 | .02 |
| | | 5 mW | 20 K | .07 |

Table I contains both the "best case" combinations of $\Delta f$, $d_B$ and $P_s$ for a research environment and combinations that would be suitable for a commercial particle counting instrument.

With a 1 Hz bandwidth, 2 $\mu m$ blur spot and 1 watt subject beam, the minimum detectable particle size is approximately $5 \times 10^{-3}$ $\mu m$. For a practical particle counting instrument, a bandwidth of at least 20 KHz is desirable to assure that randomly spaced particles are detected. Laser power should not be excessive (5 mW being reasonable), and a blur spot at least 5 times the maximum particle diameter will minimize near-miss problems. As can be seen in the Table, minimum detectable particle sizes ranges from 0.04 to 0.07 $\mu m$, with maximum particle sizes (to minimize near-misses) of 0.4 to 5.0 $\mu m$. The instrument can be provided with an adjustable blur spot to allow both low and high-end limits to be reached.

With the coherent detection hereof, there is no background signal associated with scattered light because of the interferometric configuration that is responsible for measuring the phase shift. Statistical fluctuations of molecular cluster populations below the detection limit could impart a background noise on the refractive index, but the bandwidth and other parameters will most likely dictate the lower detection limit. With intensity measurements of scattered light, on the other hand, the background scattering of the gas molecules in the viewing volume is the same order as a single 0.1 $\mu m$ particle. Thus, the detection limit of a technique based on light scattering is established at that level. Experimental configurations can reduce the background scattering and possibly lower the limit by at most a factor of two [see Hirleman, E. D., Opt. Eng'g, 19(6), 854, (1980)].

EXPERIMENTS

Figure 4:
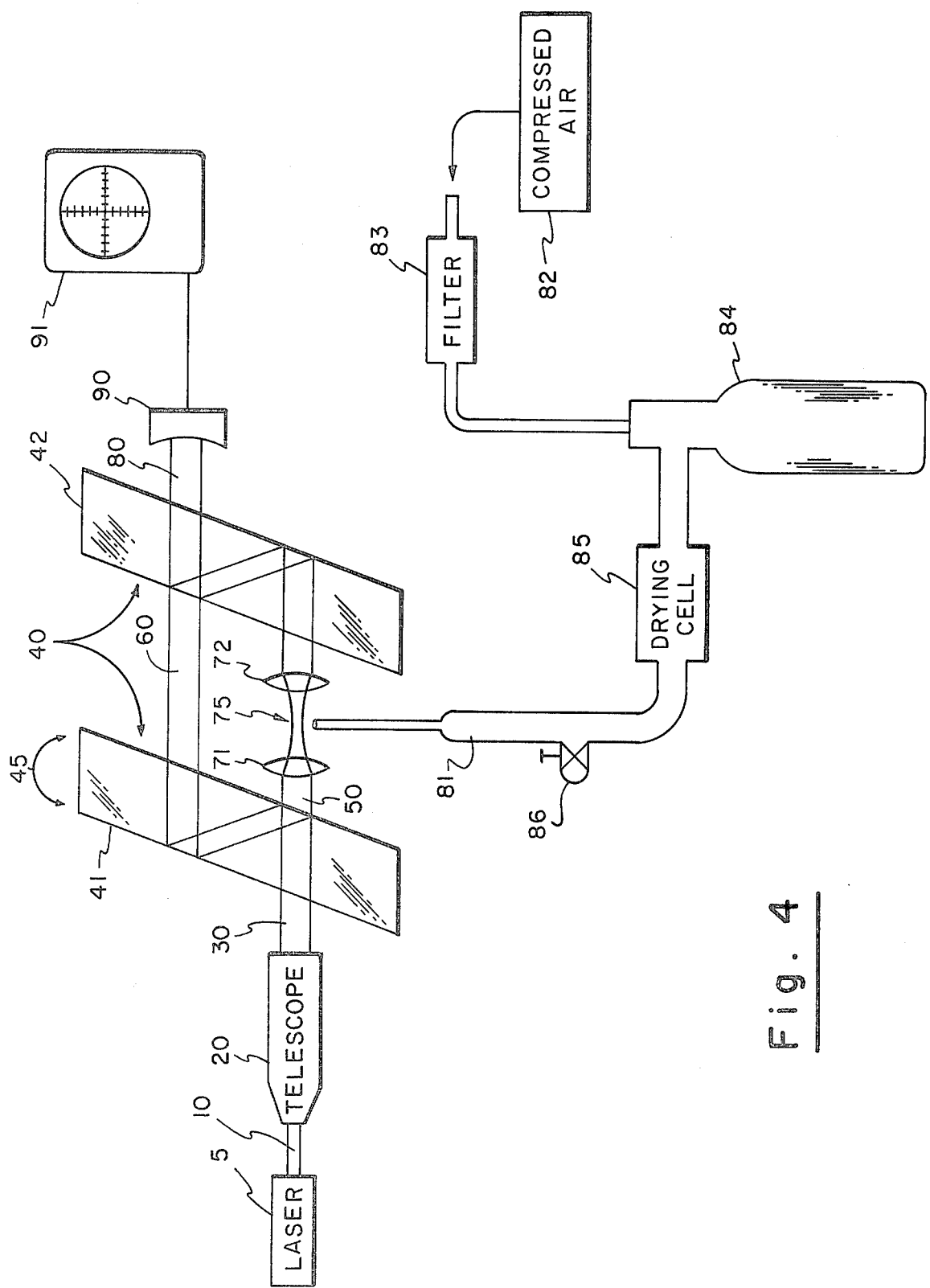
FIG. 4 is a block diagram, partially in schematic form, of an embodiment of the invention as used in performing experiments described herein.

In FIG. 4 an experimental system is shown to include elements which are the same as those of corresponding reference numerals in FIG. 1. A 5× microscope objective is used as the primary lens and a 3.5× objective is used as the gathering lens in the subject beam. The primary lens provides a beam waist of 200 $\mu m$ in diameter with a waist length of 1000 $\mu m$. The gathering lens has a blur spot diameter of 20 $\mu m$ with a depth of focus of 80 $\mu m$ and is centered in the beam waist region of the primary lens. This assures a constant radial and axial intensity profile within the viewing volume. The output of photodiode 90 is coupled to an oscilloscope 91 to view the signal in the time domain. The light intensity incident on the photodiode is more than sufficient to shot noise-limit the detector. The beam-expanding telescope 20 enlarges the fringe pattern so that it can be readily seen, aiding the interferometer adjustment into quadrature. A 0.5 milliwatt helium-neon laser 5 is used with a randomly polarized beam. A glass pasteur pipette 81 with a tip diameter of 1.0 millimeter (mm) is used to direct the flow of aerosol sample through the inspection (focal point) region 75, perpendicular to the subject beam. To minimize room vibrations, the entire system is assembled on an optical bench (not shown). The calibration system for generating standard particles consists of a source of compressed air 82, a submicron filter 83, a nebulizer 84 with distilled water suspensions of standard polystyrene latex (PSL) spheres, a drying cell 85 and a flow-regulating valve 86. Calibration particles were available from 0.085 $\mu m$ to 3.0 $\mu m$ diameter. These particles were directed through the focal point region with the pipette, where faint light scattering could be seen with the eye. The signal was read from the oscilloscope for each particle size and a calibration curve established.

Figure 5:
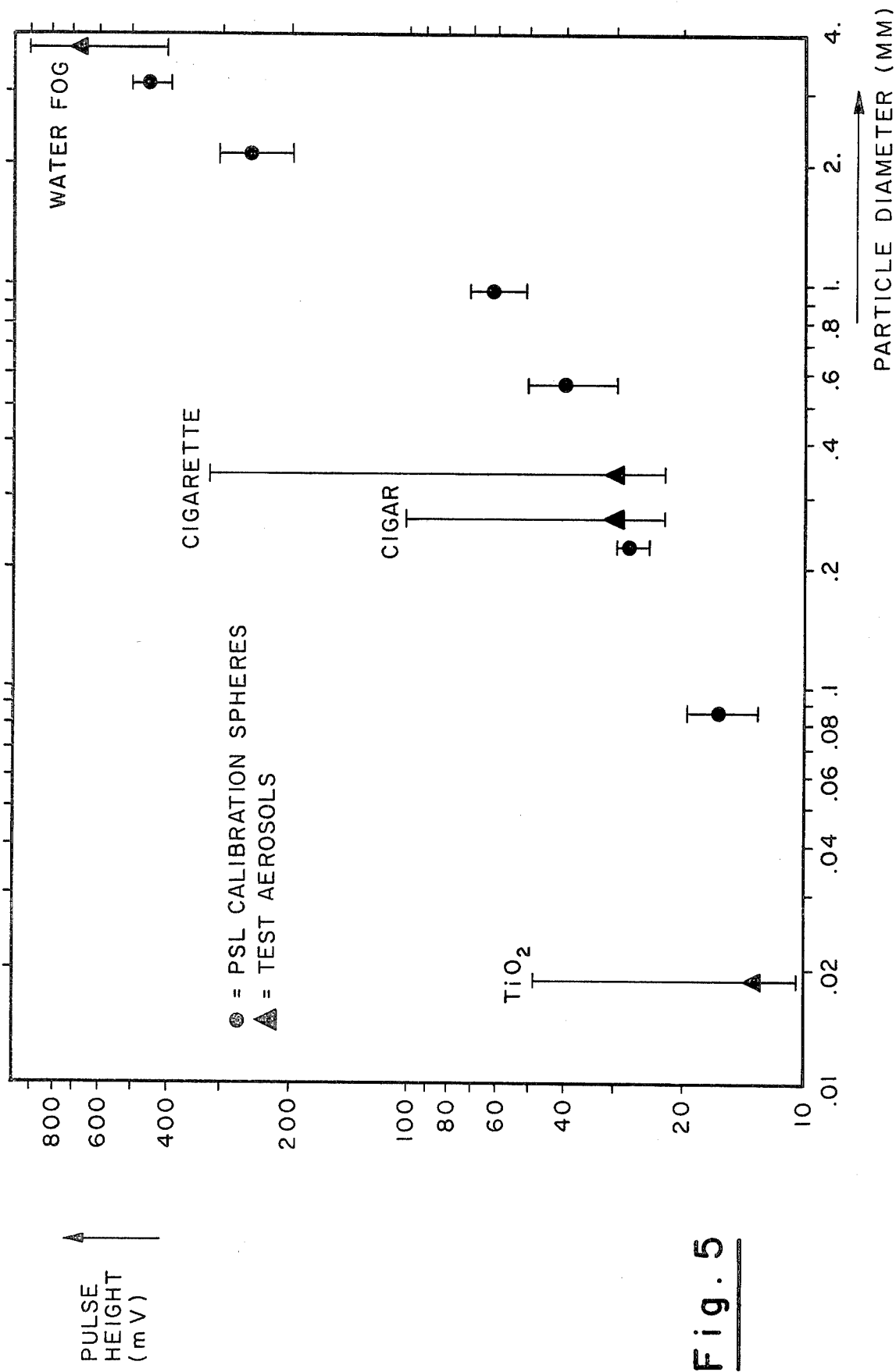
FIGS. 5-7 illustrate calibration and test results.

FIG. 5 shows the apparently monotonic calibration curve for system with signal voltage (pulse height) as function of particle diameter using PSL spheres of 0.085, 0.22, 0.55, 0.95, 2.0 and 3.0 $\mu m$. For each calibration particle, the dot indicates the most frequent pulse height, and the "error bars" indicate the minimum and maximum pulse heights seen at least once. While an absolute monotonic relationship cannot be proclaimed [see Cooke et al, App. Optics, 14(3), 734 (1975)], the signal spread observed was primarily the result of the deviation from monodispersity of the calibration aerosols. Nebulized PSL spheres can deviate markedly from a monodisperse aerosol due to trace contaminants in the liquid vehicle (distilled water) and residual surfactants present from the stock PSL suspensions. The smaller the PSL spheres, the wider the deviation.

Figure 6:
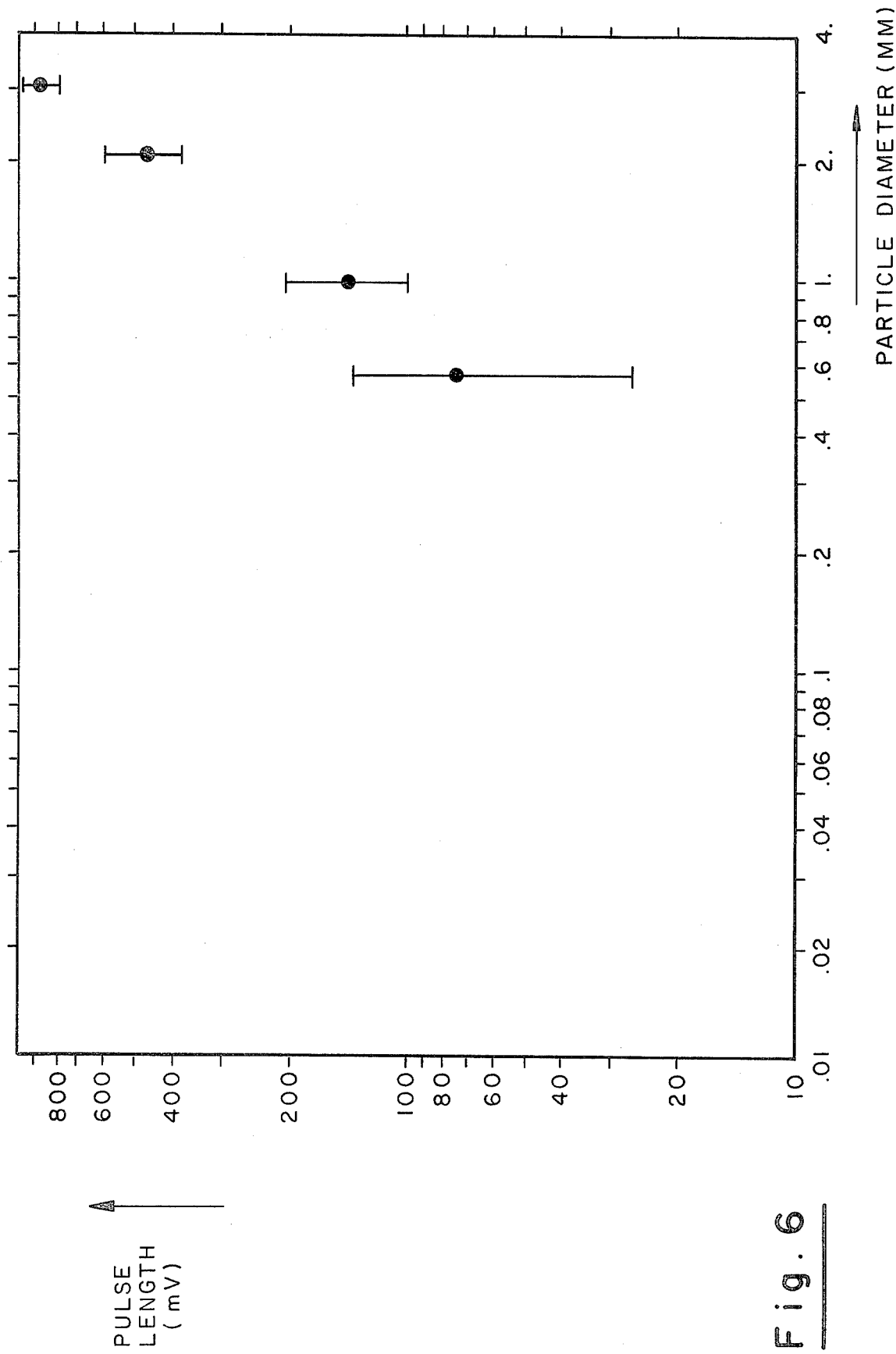

FIG. 6 shows the direct signal voltage output as a function of particle diameter for PSL spheres of 0.55, 0.95, 2.0 and 3.0 µm as measured with a Climet (Model 208) Optical Particle Counter. Using the average value to define the calibration curve, the signal spread (shown by error bars about the average) can be used to estimate the size range of each calibration aerosol. The same procedure can be done with the present system calibration curve (FIG. 6) and Table II and compares these size range. As can be seen from Table II, the size range for each calibration aerosol is of the same order for both instruments.

TABLE II

| | Particle Size Ranges for PSL Calibration Aerosols | | | | | |
|---|---|---|---|---|---|---|
| | Particle Size Range (µm) about PSL Diameter (µm) | | | | | |
| Instrument | 0.085 | 0.22 | 0.55 | 0.95 | 2.0 | 3.0 |
| FIG. 4 System | ($\approx$0.035)–0.13 | 0.18–0.30 | 0.26–0.78 | 0.78–1.1 | 1.8–2.2 | 2.8–($\approx$3.2) |
| Climet OPC (Model 208) | — | — | ($\approx$0.3)–1.0 | 0.7–1.3 | 1.8–2.5 | 2.8–($\approx$3.2) |

The system of FIG. 4 was also used to measure "unknown" test aerosols of tobacco smokes, titanium dioxide smokes and water droplet fogs. The approximate average pulse heights, as well as the spread in pulse heights measured, are also shown in FIG. 5. Mouth drawn cigarette and cigar smoke were blown through a silica gel drying cell and into the focal point region. The average pulse height for both tobacco smokes, according to the PSL calibration, correspond to a particle diameter of approximately 0.3 µm. The cigar smoke distribution ranged from 0.1 to 1.0 µm while the cigarette smoke was found to be between 0.1 to 2.0 µm. The generally accepted size range for tobacco smoke is between 0.01 and 1.0 µm [see Perkins "Air Pollution" p. 225, McGraw Hill, 1974]. Also measured by the system was nebulized distilled water fog. The average pulse height fell above the largest PSL sphere, with a pulse-height spread corresponding to particles greater than 3.0 µm diameter. The water fog was measured by the Climet CI-208 OPC to be predominantly 5 µm and larger.

Figure 7:
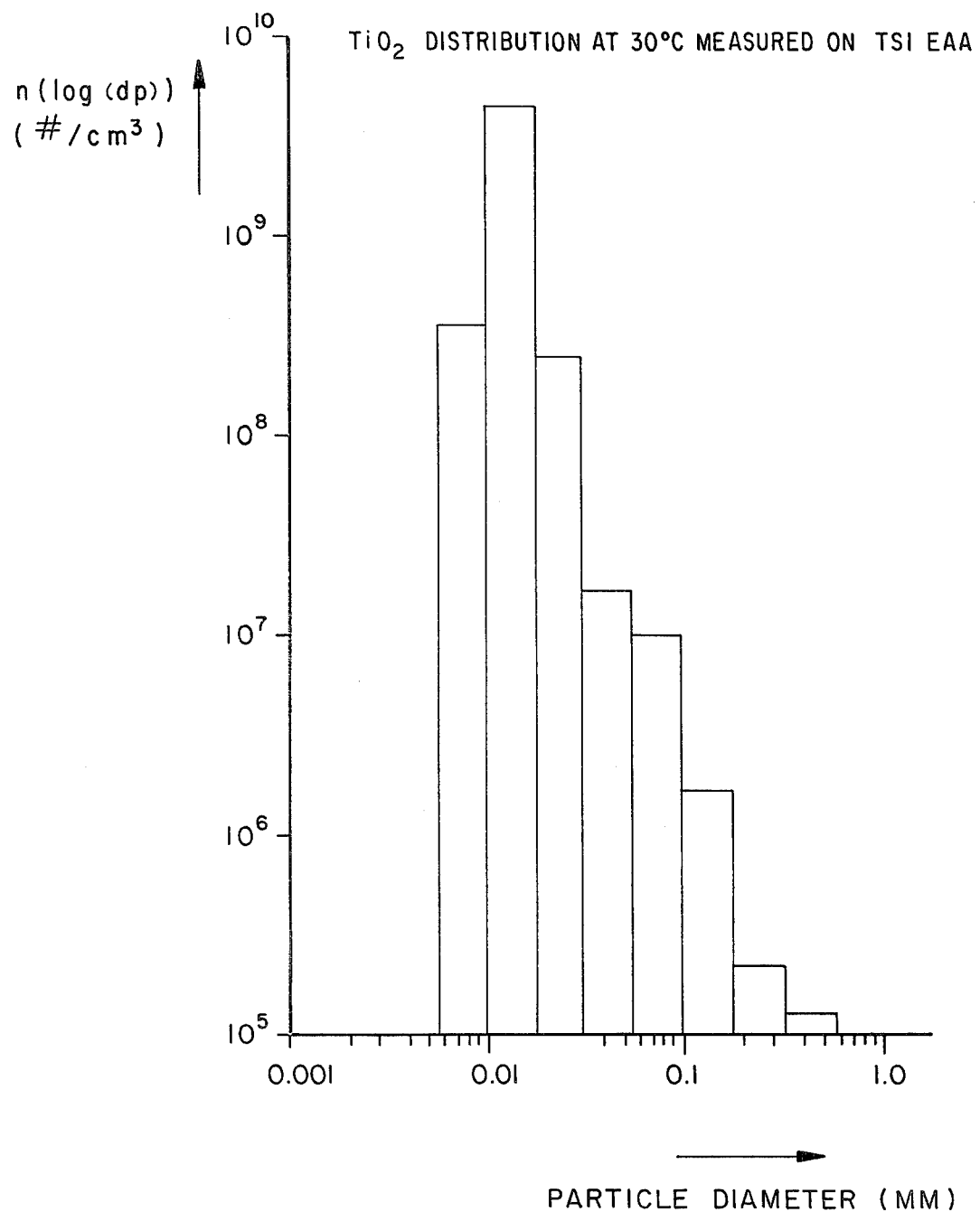

Refractory particles of titanium dioxide (TiO$_2$) were made by reacting titanium tetrachloride with room-temperature air. A TSI, Inc. (Model 3030) electrical aerosol analyzer (EAA) was used to establish the TiO$_2$ distribution as shown in FIG. 7. The TiO$_2$ aerosol consisted of small particles with diameters ranging from 0.005 to 0.5 µm. A single mode was found in the interval between 0.01 and 0.02 µm, and was at least an order of magnitude (in number concentration) greater than any other size interval. Shown on FIG. 5 is the average pulse height generated by the TiO$_2$ aerosol on the FIG. 4 system. The average pulse height fell below the smallest (0.085 µm) PSL calibration sphere and was placed on FIG. 5 between 0.01 and 0.02 µm, based on the EAA distribution in FIG. 7. The signal spread from the TiO$_2$ aerosol ranged from the background noise of the system to a value that corresponds to a particle diameter of 0.7 to 0.8 µm.

In order to test the in-situ capabilities of the present system, a fuel rich laminar diffusion flame of natural gas was stabilized in a 20 mm diameter Pyrex glass chimney. When the flame was placed in the focal point region of the system, as shown in FIG. 8, the interferometer could be readjusted into quadrature over the receptor area of the photodetector, even though the fringe pattern was distorted on the edges by the cylindrical geometry of the chimney.

Titanium tetrachloride was then introduced into the natural gas stream and the size of titanium dioxide particles produced in the flame zone were measured. The pulses fell in the same size range as was previously determined for titanium dioxide, but visual inspection of the signals indicated more frequent pulses in the larger range than seen for TiO$_2$ formation at room temperature.

The present invention is seen to have the advantage of allowing sizing of particles over a wide range of sizes with a single technique. Also, the invention can be adapted for in-situ measurement conditions. A further advantage of the invention is that only light that is coherently superimposed with the local oscillator beam will contribute to the power measured in the phase modulated sidebands. Consequently, light scattered by particles outside of the viewing volume, room lights, window lights and light from emission within the volume (such as a flame zone) will contribute only to additive noise superimposed on the particle signals. This noise will consist of DC terms and low frequency AC terms which can be filtered out electronically, since the particle signal frequencies are much greater than those of the stray light.

A still further advantage of the present invention is the relatively high particle concentrations that can be handled, sample dilution not being necessary in many cases. The present technique assumes that only one particle at a time passes through an optical viewing volume defined by the resolution limit and depth of focus of the gathering lens. Concidence errors will result if this is not the case, and the total aerosol density must be low enough to make this problem statistically insignificant. A conservative estimate of the count loss due to coincidence is summarized by Whitby and Willeke ["Aerosol Measurement" U. of Florida Press (1979)] as $$N_i/N_t = \exp(-N_t v) \quad (19)$$

where $N_i$ and $N_t$ are the indicated and actual particle concentrations respectively, and the optical viewing volume is given by v. Table III shows the maximum allowable number concentration for varying blur-spot diameters, assuming no more than 5% coincidence loss.

TABLE III

| Total Allowable Number concentrations for coincidence error of less than 5% | | | |
|---|---|---|---|
| $d_B$[µm] | $Z_B$[µm] | $N_{tot}$ | [#/cm$^3$] |
| 2 | $\approx$5 | | 10$^9$ |
| 5 | $\approx$15 | | 10$^8$ |
| 25 | $\approx$100 | | 10$^6$ |

The invention has been described with reference to a particular embodiment, but variations within the spirit and scope of the invention will occur to those skilled in the art. For example, it will be understood that alternative techniques for separating and/or combining the subject and reference beams can be implemented, as can alternative techniques for focusing and/or gathering. Also, a portion of the subject beam which is not subjected to a particle can be used as the equivalent of a reference beam.

We claim:

1. Apparatus for sizing individual particles passing through an inspection region, comprising:
   means for generating a collimated coherent beam of light;
   means for separating said beam into a subject beam and a reference beam;
   means for focusing the subject beam at the inspection region;
   means for gathering light from the inspection region;
   means for combining the gathered light and the reference beam;
   photodetection means responsive to the combined light for producing an electrical signal representative of the gathered light;
   means for determining the phase shift of light scattered from an individual particle passing through the inspection region by measuring the power in the phase modulated sidebands of said electrical signal, said phase shift being indicative of the size of the particle passing through the inspection region; and
   means for counting pulses resulting from said phase shifted sidebands to obtain a count of particles passing through the inspection region.

2. Apparatus as defined by claim 1 wherein said gathering means is adapted to receive substantially only near-forward light from the inspection region.

3. Apparatus as defined by claim 1, wherein said focusing means and said gathering means respectively comprise a pair of spaced lenses in the path of the subject beam.

4. Apparatus as defined by claim 2, wherein said focusing means and said gathering means respectively comprise a pair of spaced lenses in the path of the subject beam.

5. A method for sizing individual particles passing through an inspection region, comprising the steps of:
   generating a collimated coherent beam of light;
   separating said beam into a subject beam and reference beam;
   focusing the subject beam at the inspection region;
   gathering light from the inspection region;
   combining the gathered light and the reference beam;
   producing electrical signals representative of the combined light;
   determining the phase shift of light scattered from an individual particle passing through the inspection region by measuring the power in the phase modulated sidebands of said electrical signal, said phase shift being indicative of the size of the particle passing through the inspection region; and
   counting pulses resulting from said phase shifted sidebands to obtain a count of particles passing through the inspection region.

6. The method as defined by claim 5 wherein said gathering step comprises receiving substantially only near-forward light from the inspection region.

7. The method as defined by claim 5, wherein said focusing and gathering steps employ a pair of spaced lenses in the path of the subject beam.

8. The method as defined by claim 6, wherein said focusing and gathering steps employ a pair of spaced lenses in the path of the subject beam.

9. A method for sizing particles, comprising the steps of:
   directing individual particles through an inspection region;
   generating a collimated coherent beam of light;
   focusing the beam at the inspection region;
   gathering light from the inspection region;
   producing electrical signals representative of the gathered light; and
   determining, from said electrical signals, the phase shift of light scattered from an individual particle passing through the inspection region, said phase shift being indicative of the size of the particle passing through the inspection region.

10. Apparatus for sizing particles, comprising:
    means for directing individual particles through an inspection region;
    means for generating a collimated coherent beam of light;
    means for separating said beam into a subject beam and a reference beam;
    means for focusing the subject beam at the inspection region;
    means for gathering light from the inspection region;
    means for combining the gathered light and the reference beam;
    photodetection means responsive to the combined light for producing an electrical signal representative of the gathered light; and
    means for determining the phase shift of light scattered from an individual particle passing through the inspection region by measuring the power in the phase modulated sidebands of said electrical signal, said phase shift being indicative of the size of the particle passing through the inspection region.

11. Apparatus as defined by claim 10, wherein said gathering means is adapted to receive substantially only near-forward light from the inspection region.

12. Apparatus as defined by claim 11, wherein said focusing means and said gathering means respectively comprise a pair of spaced lenses in the path of the subject beam.

13. Apparatus as defined by claim 10 wherein, said focusing means and said gathering means respectively comprise a pair of spaced lenses in the path of the subject beam.

14. Apparatus as defined by claim 10, further comprising means for counting pulses resulting from said phase shifted sidebands to obtain a count of particles passing through the inspection region.

15. A method for sizing particles, comprising the steps of:
    directing individual particles through an inspection region;
    generating a collimated coherent beam of light;
    separating said beam into a subject beam and a reference beam;
    focusing the subject beam at the inspection region;
    gathering light from the inspection region;
    combining the gathered light and the reference beam;

producing electrical signals representative of the combined light; and determining the phase shift of light scattered from an individual particle passing through the inspection region by measuring the power in the phase modulated sidebands of said electrical signal, said phase shift being indicative of the size of the particle passing through the inspection region.

16. The method as defined by claim 15, wherein said gathering step comprises receiving substantially only near-forward light from the inspection region.

17. The method as defined by claim 16 wherein said focusing and gathering steps employ a pair of spaced lenses in the path of the subject beam.

18. The method as defined by claim 15, wherein said focusing and gathering steps employ a pair of spaced lenses in the path of the subject beam.

19. The method as defined by claim 15, further comprising the step of counting pulses resulting from said phase shifted sidebands to obtain a count of particles passing through the inspection region.

* * * * *